(12) United States Patent
Hwang et al.

(10) Patent No.: US 9,241,671 B2
(45) Date of Patent: Jan. 26, 2016

(54) APPARATUS AND METHOD FOR REMOVING NOISE FROM BIOSIGNALS

(71) Applicant: Industry-Academic Cooperation Foundation, Yonsei University, Seoul (KR)

(72) Inventors: Do-Sik Hwang, Seoul (KR); Ung Jang, Seoul (KR); Ji-han Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 13/777,433

(22) Filed: Feb. 26, 2013

(65) Prior Publication Data

US 2013/0245479 A1  Sep. 19, 2013

(30) Foreign Application Priority Data

Mar. 13, 2012 (KR) .................. 10-2012-0025515

(51) Int. Cl.
*A61B 5/00* (2006.01)
*A61B 5/0456* (2006.01)

(52) U.S. Cl.
CPC ............. *A61B 5/7203* (2013.01); *A61B 5/7246* (2013.01); *A61B 5/0456* (2013.01)

(58) Field of Classification Search
CPC .. A61B 5/0452; A61B 5/0456; A61B 5/0472; A61B 5/04012; A61B 5/7203; A61B 5/7246
USPC ................................. 600/509, 517, 321, 521
See application file for complete search history.

(56) References Cited

U.S. PATENT DOCUMENTS

| | | | | |
|---|---|---|---|---|
| 4,893,632 | A * | 1/1990 | Armington | 600/509 |
| 4,938,228 | A * | 7/1990 | Righter et al. | 600/503 |
| 4,974,602 | A * | 12/1990 | Abraham-Fuchs et al. | 600/544 |
| 5,159,932 | A * | 11/1992 | Zanetti et al. | 600/508 |
| 5,609,158 | A * | 3/1997 | Chan | 600/518 |
| 5,792,195 | A * | 8/1998 | Carlson et al. | 607/17 |
| 5,891,048 | A * | 4/1999 | Nigam et al. | 600/521 |
| 6,047,206 | A * | 4/2000 | Albrecht et al. | 600/509 |
| 7,684,854 | B2 * | 3/2010 | Park et al. | 600/509 |
| 7,826,885 | B2 * | 11/2010 | Nambu et al. | 600/407 |
| 7,894,887 | B2 * | 2/2011 | Yanai et al. | 600/509 |
| 8,380,314 | B2 * | 2/2013 | Panken et al. | 607/45 |
| 2003/0208129 | A1 * | 11/2003 | Beker et al. | 600/509 |
| 2004/0093192 | A1 * | 5/2004 | Hasson et al. | 703/1 |
| 2004/0260188 | A1 * | 12/2004 | Syed et al. | 600/509 |
| 2005/0222513 | A1 * | 10/2005 | Hadley et al. | 600/515 |
| 2006/0276716 | A1 * | 12/2006 | Healey et al. | 600/516 |
| 2007/0066907 | A1 * | 3/2007 | Beker et al. | 600/509 |
| 2007/0233196 | A1 * | 10/2007 | Stadler et al. | 607/4 |
| 2007/0239046 | A1 * | 10/2007 | Ghanem et al. | 600/509 |
| 2007/0255152 | A1 * | 11/2007 | Park et al. | 600/513 |
| 2008/0171943 | A1 * | 7/2008 | Farringdon et al. | 600/509 |

(Continued)

*Primary Examiner* — Christopher A Flory (57) ABSTRACT

Disclosed are an apparatus and a method for removing noise from biosignals. An embodiment of the invention provides an apparatus for removing noise from biosignals measured for a particular period of time that includes: a similarity calculating unit configured to calculate a similarity between any one biosignal from among the biosignals and other biosignals; and a noise removal unit configured to remove noise from the any one biosignal by using the similarity. Aspects of the invention provide the advantage of effectively removing noise from biosignals without distorting the waveforms of the biosignals.

10 Claims, 12 Drawing Sheets
(3 of 12 Drawing Sheet(s) Filed in Color)

(56) References Cited

U.S. PATENT DOCUMENTS

| | | | |
|---|---|---|---|
| 2008/0177193 A1* | 7/2008 | Farringdon et al. | 600/509 |
| 2008/0183082 A1* | 7/2008 | Farringdon et al. | 600/481 |
| 2008/0183090 A1* | 7/2008 | Farringdon et al. | 600/509 |
| 2008/0243013 A1* | 10/2008 | Yanai et al. | 600/509 |
| 2009/0192394 A1* | 7/2009 | Guttag et al. | 600/509 |
| 2010/0016747 A1* | 1/2010 | Serra Autonell | 600/523 |
| 2010/0094147 A1* | 4/2010 | Inan et al. | 600/500 |
| 2010/0113953 A1* | 5/2010 | Marcovecchio et al. | 600/515 |
| 2010/0286532 A1* | 11/2010 | Farringdon et al. | 600/483 |
| 2012/0101357 A1* | 4/2012 | Hoskuldsson et al. | 600/382 |
| 2012/0123232 A1* | 5/2012 | Najarian et al. | 600/345 |
| 2012/0245439 A1* | 9/2012 | Andre et al. | 600/310 |
| 2013/0046193 A1* | 2/2013 | Guttag et al. | 600/509 |
| 2013/0245479 A1* | 9/2013 | Hwang et al. | 600/521 |

* cited by examiner

APPARATUS AND METHOD FOR REMOVING NOISE FROM BIOSIGNALS

CROSS-REFERENCE TO RELATED APPLICATIONS

This application claims the benefit of Korean Patent Application No. 10-2012-0025515 filed on Mar. 13, 2012, the disclosure of which is incorporated herein by reference in its entirety.

TECHNICAL FIELD

The embodiments of the present invention relate to an apparatus and a method for removing noise from biosignals, more particularly to an apparatus and a method for removing noise from biosignals based on similarity between the biosignals.

BACKGROUND ART

Electrocardiogram (ECG) signals are electrical signals that originate from the heart and are important in diagnosing and monitoring heart conditions. With the advent of e-health and u-health programs, etc., in recent times, there is an interest in technology for measuring ECG signals in a mobile environment.

A major problem for measuring ECG signals in a mobile environment is low signal-to-noise ratio (hereinafter, "SNR"). In a typical hospital, ECG signals are measured for a stable posture in a stable environment using high-performance equipment, but in a mobile environment, the ECG measurement may be performed for a subject that is not always in a stable posture, and the equipment used may be a compact device that provides a relatively low performance.

For ECG signals obtained in such an environment, it may not be possible to sufficiently remove noise using conventional, typical noise removal methods.

That is, conventional ECG noise removal methods can be divided mainly into methods that use general high/band/low pass filters and methods that use wavelets. These conventional methods are effective when applied to signals having a somewhat high SNR, but if they are applied to ECG signals having a low SNR and noise is removed excessively, the shapes of waveforms such as the QRS-complex, P-wave, T-wave, etc., essential in diagnosing a human body, may be greatly altered.

SUMMARY

To resolve the problems of the related art, an aspect of the invention provides an apparatus and a method for effectively removing noise from biosignals measured at a mobile device.

Other objectives of the invention can be derived by those skilled in the art from the embodiments of the invention described below.

To achieve the objectives above, an embodiment of the invention provides an apparatus for removing noise from biosignals measured for a particular period of time. The apparatus includes: a similarity calculating unit configured to calculate a similarity between any one biosignal from among the biosignals and other biosignals; and a noise removal unit configured to remove noise from the any one biosignal by using the similarity.

The noise removal unit can calculate weights for the other biosignals respectively by using the similarity and can remove noise from the any one biosignal based on a weighted average of the biosignals using the weights.

The biosignal can include an ECG (electrocardiogram) signal, and the ECG signal can include a P-wave, a QRS-complex, and a T-wave waveform.

The apparatus can further include a selection unit configured to select a particular target signal for the noise removal from among signals included in the any one biosignal.

The similarity calculating unit can include: an alignment unit configured to align the biosignals with respect to an R peak of the QRS complex waveform included in the biosignals; a search window setting unit configured to set a range of a search window to include the target signal and signals within a particular range centering around the target signal from among signals included in the aligned biosignals; a unit window setting unit configured to set a size of a unit window for the calculating of similarity; and a calculating unit configured to calculate a similarity between signals included in a unit window centering around the target signal and signals included in unit windows centering around signals included in the search window.

The alignment unit can separate the biosignals based on a preset area centering around the R peak and can align the separated biosignals with respect to the R peak.

The calculating unit can calculate the similarity by using a mean absolute deviation between the signals included in a unit window centering around the target signal and the signals included in unit windows centering around signals included in the search window.

The search window setting unit can set the range of the search window differently according to a type of waveform to which the selected target signal belongs, and the unit window setting unit can set the size of the unit window differently according to a type of waveform to which the selected target signal belongs.

The noise removal unit can include: a weight calculating unit configured to calculate weights for signals included in the search window respectively by using the similarity; and a weighted averaging unit configured to perform a weighted averaging for signals included in the search window by using the weights.

Another embodiment of the invention provides a method for removing noise from biosignals measured for a particular period of time. The method includes: calculating a similarity between any one biosignal from among the biosignals and other biosignals; and removing noise from the any one biosignal by using the similarity.

The biosignal can be an ECG (electrocardiogram) signal including a P-wave, a QRS-complex, and a T-wave waveform.

Calculating the similarity can include: aligning the biosignals with respect to an R peak of the QRS complex waveform included in the biosignals; selecting a particular target signal for the noise removal from among signals included in the any one biosignal; setting a range of a search window to include the target signal and signals within a particular range centering around the target signal from among signals included in the aligned biosignals; setting a size of a unit window for the calculating of similarity; and calculating a similarity between signals included in a unit window centering around the target signal and signals included in unit windows centering around signals included in the search window.

Aspects of the invention provide the advantage of effectively removing noise from biosignals without distorting the waveforms of the biosignals.

Additional aspects and advantages of the present invention will be set forth in part in the description which follows, and in part will be obvious from the description, or may be learned by practice of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

As the present invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In the written description, certain detailed explanations of related art are omitted when it is deemed that they may unnecessarily obscure the essence of the present invention. In describing the drawings, similar reference numerals are used for similar elements.

Certain embodiments of the present invention will be described below in more detail with reference to the accompanying drawings.

Biosignals are signals created in the human body and can be used to check a person's health. Examples of biosignals include pulse signals, ECG (electrocardiogram) signals, etc.

Biosignals, which are created in the body repeatedly in accordance with the beating of the heart, tend to have similar waveforms. A principle of the invention is remove noise from biosignals by using this similarity in biosignals.

Figure 1:
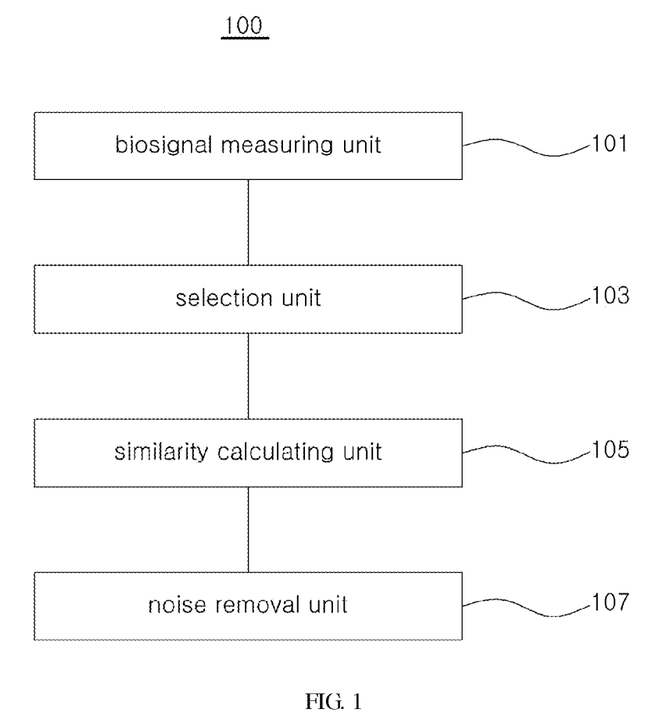
FIG. 1 is a block diagram illustrating the composition of an apparatus for removing noise from biosignals according to an embodiment of the invention.

FIG. 1 is a block diagram illustrating the composition of an apparatus for removing noise from biosignals according to an embodiment of the invention.

Referring to FIG. 1, the noise removal apparatus 100 can include a biosignal measuring unit 101, a selection unit 103, a similarity calculating unit 105, and a noise removal unit 107.

The biosignal measuring unit 101 may measure the biosignals, which are created repeatedly in the body and which have similar waveforms, for a particular period of time. For example, the biosignal measuring unit 101 can receive signals detected by sensors attached to a part of the body, in order to measure the biosignals. Of course, various other embodiments can be employed by which the user directly uses a mobile device for measuring biosignals. As this is not the key feature of the invention, further descriptions on this matter will be omitted.

The selection unit 103 may select any one biosignal from which to remove noise, from among the biosignals measured by the biosignal measuring unit 101 for a particular period of time.

The similarity calculating unit 105 may calculate a similarity between the any one biosignal, selected by the selection unit 103 from among the biosignals measured for the particular period of time, and the other biosignals.

Then, the noise removal unit 107 may remove noise from the any one biosignal, using the similarity between the any one biosignal and other biosignals.

For example, the noise removal unit 107 can calculate weights for the other biosignals, respectively, using the similarity, and can remove noise from the any one biosignal based on the weighted average of the biosignals using the weights.

Thus, by repeating the noise removal process for all of the biosignals measured for a particular period of time, the noise removal apparatus 100 can remove noise from the biosignals.

For convenience, it will be assumed in the descriptions below that the biosignals are ECG signals, but it would be obvious to those skilled in the art that the biosignals are not limited to ECG signals.

Figure 2:
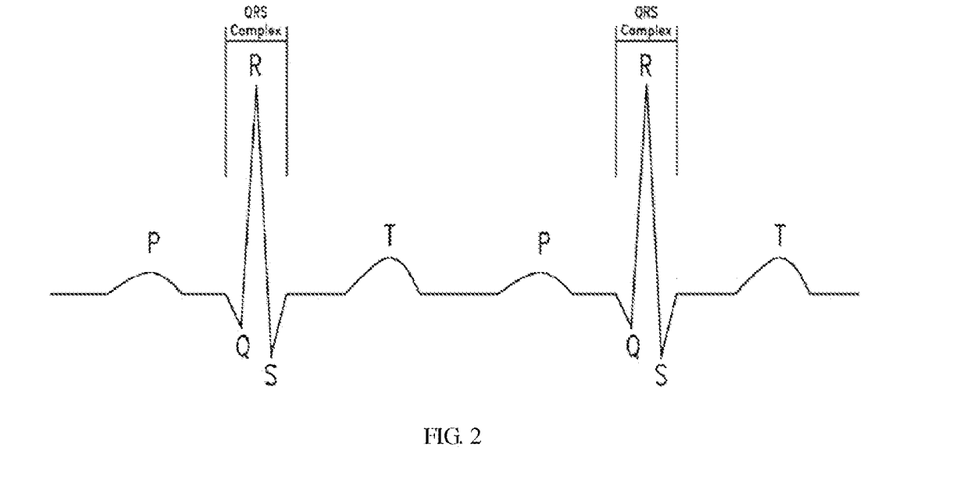
FIG. 2 illustrates an example of an ECG signal.

FIG. 2 illustrates an example of an ECG signal.

Referring to FIG. 2, an ECG signal is a measured value of the action current created by the heart muscles in accordance with the beating of the heart. The ECG signal includes a P-wave, a QRS-complex, and a T-wave waveform; in the body, the ECG signals including the three types of waveforms above are created in repetition.

The QRS-complex waveform, which includes an R peak, may be measured in a short amount of time, while the P-wave and the T-wave maybe measured with relatively smaller current values in longer periods of time compared to the QRS-complex waveform.

According to an embodiment of the invention, the noise removal apparatus 100 can remove noise considering the waveform of the ECG signal, and to this end, the selection unit 103 can select any one biosignal from among the biosignals measured for a particular period of time and can select a particular target signal 401 for noise removal from among the signals included in the any one biosignal.

Also, the noise removal apparatus 100 can perform the noise removal considering which waveform the particular target signal 401 selected by the selection unit 103 belongs to. This aspect will be described later in further detail.

Figure 3:
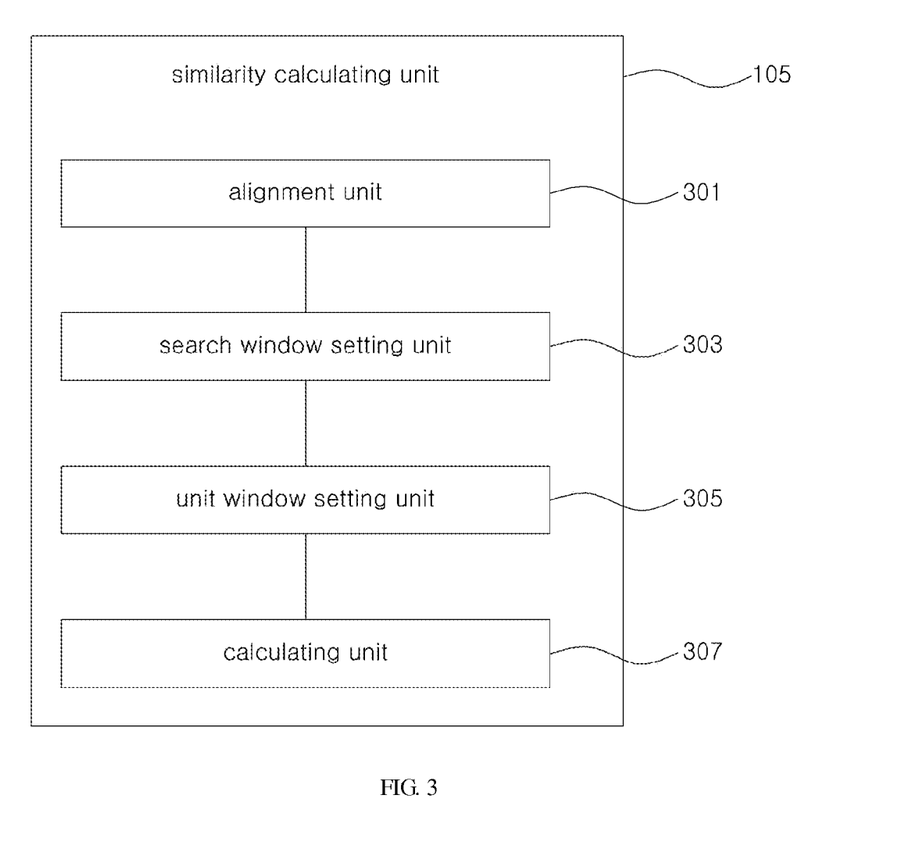
FIG. 3 is a block diagram illustrating the detailed composition of a similarity calculating unit according to an embodiment of the invention.

FIG. 3 is a block diagram illustrating the detailed composition of a similarity calculating unit according to an embodiment of the invention.

Referring to FIG. 3, the similarity calculating unit 105 can include an alignment unit 301, a search window setting unit 303, a unit window setting unit 305, and a calculating unit 307.

The alignment unit 301 may align the biosignals with respect to the R peak of the QRS-complex waveform included in each biosignal. To this end, the alignment unit 301 can separate the biosignals measured for a particular period of time based on a preset area centering around the R peak, and can align the separated biosignals with respect to the R peak. Here, the preset area may refer to an area including the P-wave and the T-wave waveforms centering around the QRS-complex waveform.

Figure 4:
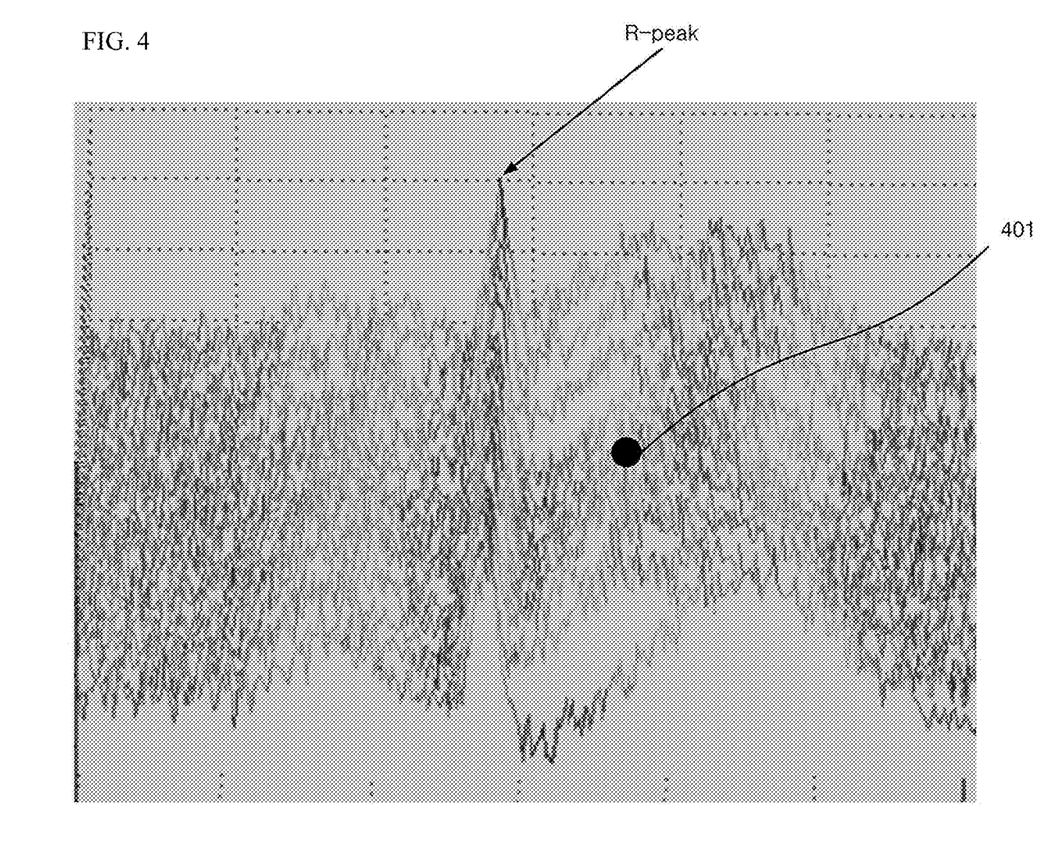
FIG. 4 illustrates an example of biosignals aligned according to an embodiment of the invention.

FIG. 4 illustrates an example of biosignals aligned according to an embodiment of the invention.

In FIG. 4, it can be seen that the biosignals measured by the alignment unit 301 for a particular period of time have been aligned with respect to the R peak, and the selection unit 103 can select a particular target signal 401, from which to remove noise, from among the aligned biosignals.

According to an embodiment of the invention, the selection unit 103 can select a particular target signal 401 from signals that belong to any one of the P-wave, QRS-complex, and T-wave waveforms, from among the signals included in the biosignals.

Referring again to FIG. 3, the search window setting unit 303 may set the range of a search window, by which to calculate the similarities for the aligned biosignals.

To be more specific, the search window setting unit 303 may set the range of the search window to include the target signal 401 and the signals that lie within a particular range centering around the target signal 401, from among the signals included in the aligned biosignals.

Figure 5:
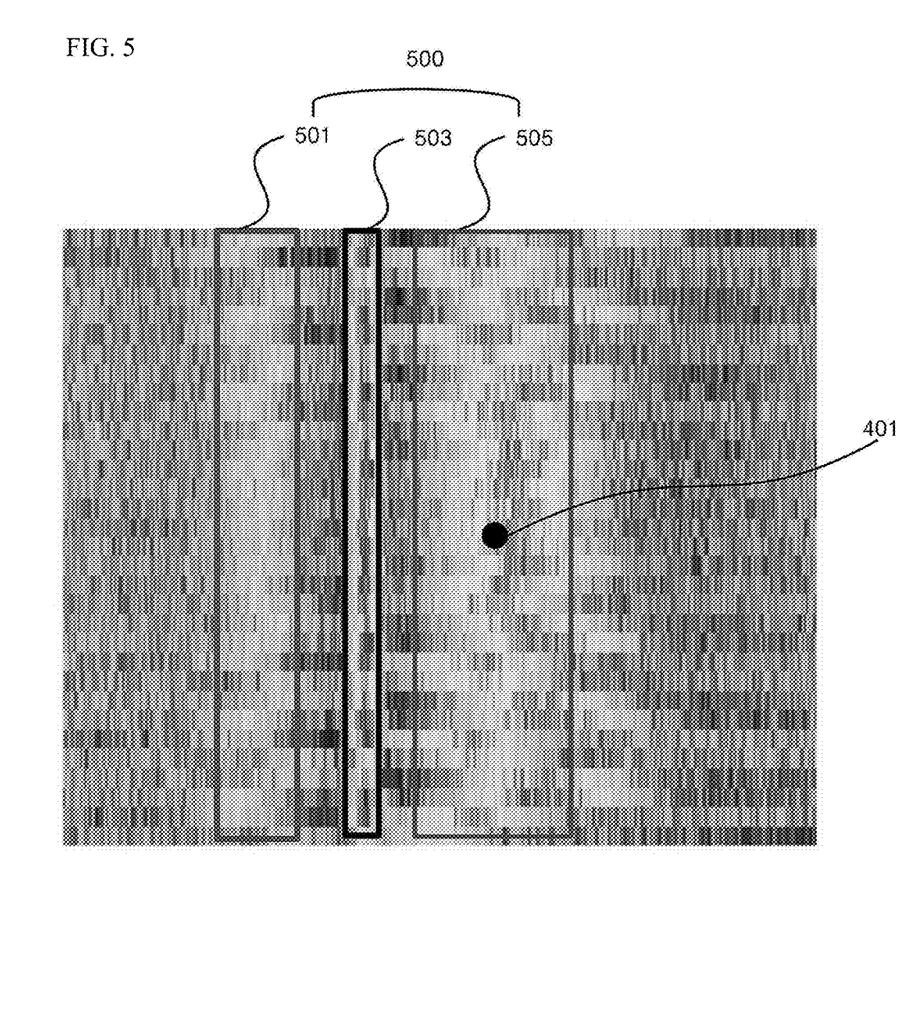
FIG. 5 illustrates an example of setting a search window according to an embodiment of the invention.

FIG. 5 illustrates an example of setting a search window according to an embodiment of the invention.

FIG. 5 illustrates portions of the aligned biosignals, and the search window setting unit 303 may set the range of the search window 500 for calculating the similarities between the biosignals aligned as shown in FIG. 5.

According to an embodiment of the invention, the search window setting unit 303 can set the range of the search window, i.e. the position and size of the search window 500, according to the type of waveform to which the target signal 401 belongs. For example, the search window setting unit 303 can select the range of a first search window 501 to include the P-wave waveform region from among the aligned biosignals if the target signal 401 belongs to the P-wave waveform, and can select the range of a second search window 503 to include the QRS-complex waveform region if the target signal 401 belongs to the QRS-complex waveform. Also, if the target signal 401 belongs to the T-wave waveform, the range of a third search window 505 can be set to include the T-wave waveform region.

Since the QRS-complex waveform is measured for a relatively shorter amount of time than for the P-wave and T-wave waveforms, the size of the second search window 503 along direction of the lateral axis can be set smaller than the lateral direction sizes of the search windows 501, 505 for the other waveforms. That is, the search window setting unit 303 can set the range of the search window 500 according to the type of waveform, considering the length of time during which the waveform is measured.

Referring again to FIG. 3, the unit window setting unit 303 may set the size of a unit window for calculating similarity.

Then, the calculating unit 307 may calculate the similarities between the signals included in the unit window centering around the target signal 401 and the signals included in unit windows centering around signals included in the search window.

Figure 6:
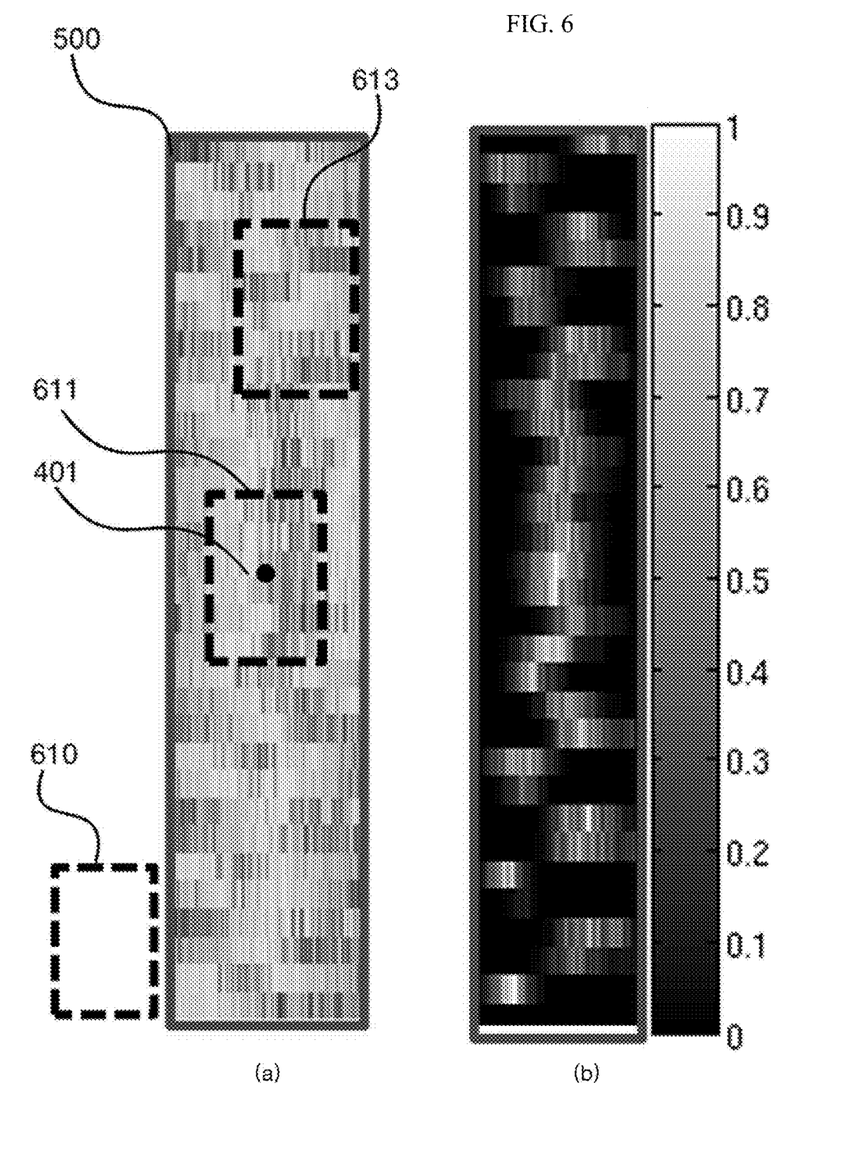
FIG. 6 illustrates an example of calculating similarity by using a search window and unit windows according to an embodiment of the invention.

FIG. 6 illustrates an example of calculating similarity by using a search window and unit windows according to an embodiment of the invention.

Where drawing (a) of FIG. 6 is a magnified view of the region of the third search window 505, the unit window setting unit 303 may set the size of the unit window 610 for calculating similarity. According to an embodiment of the invention, the size of the unit window 610 can also be set differently according to the type of waveform, as is the case for the size of the search window 500.

The calculating unit 307 may calculate the similarities between the signals included in the unit window (hereinafter referred to as the "first unit window 611") centering around the target signal 401 and the signals included in the unit windows (hereinafter referred to as "second windows 613") respectively centering around signals included in the search window 610.

According to an embodiment of the invention, the target signal 401 from which to remove noise can be denoted $I_R$, and the signals included in a search window 500 of a particular section centering around the target signal can be denoted $I_1 \ldots I_n \ldots I_N$. Also, the k number of signals included in the first unit window 611 centering around the target signal $I_R$ can be denoted $B^R = [B^R_1, B^R_2, \ldots, B^R_k]$, while the k number of signals included in the second unit windows 613 centering around the remaining signals $I_1 \sim I_N$, respectively, can be denoted $B^n = [B^n_1, B^n_2, \ldots, B^n_k]$, $n=1 \ldots N$.

In this case, the calculating unit 307 can perform the similarity calculations between the target signal $I_R$ targeted for noise removal and the remaining signals $I_1 \ldots I_n \ldots I_N$ by using the sum of absolute deviation (SAD) between the first unit window 611 and the second unit window 613 for each of the remaining signals. The similarity calculation can also be performed by using MSE, correlation, etc., besides SAD.

For example, the similarity between $I_R$ and $I_n$ can be expressed as Equation 1 below.

$$SAD_n = \Sigma |B^R - B^n| = \Sigma_{i=1}^{k} |B_i^R - B_i^n| \qquad \text{[Equation 1]}$$

Here, $SAD_n$ represents the similarity between $I_R$ and $I_n$, where a smaller value means greater similarity.

Drawing (b) of FIG. 6 shows weights for the signals calculated by using the similarities; a description of the weights will be provided below with reference to FIG. 7. A darker color (i.e. nearing 0) represents low similarity, while a lighter color (i.e. nearing 1) represents high similarity.

Figure 7:
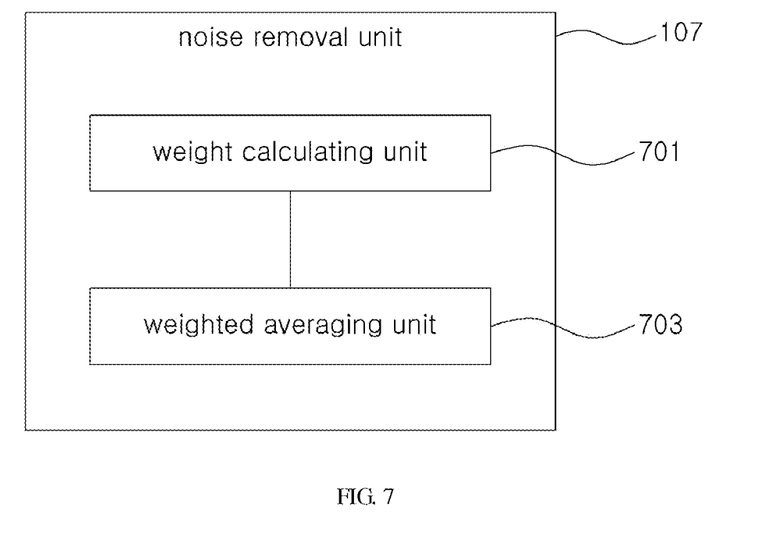
FIG. 7 is a block diagram illustrating the detailed composition of a noise removal unit according to an embodiment of the invention.

FIG. 7 is a block diagram illustrating the detailed composition of a noise removal unit according to an embodiment of the invention.

Referring to FIG. 7, the noise removal unit 107 can include a weight calculating unit 701 and a weighted averaging unit 703.

Based on the similarities between the target signal 401 and the remaining signals as calculated by Equation 1, the weight calculating unit 701 may calculate the weights used for the weighted averaging, such as by Equation 2 shown below.

$$w_n = e^{-SAD_n/\beta} \qquad \text{[Equation 2]}$$

Here, $w_n$ is the weight for signal $I_n$, and $\beta$ is a constant for adjusting the degree of noise removal.

The weight calculating unit 701 may use Equation 2 to calculate weights for all of the signals $I_1 \ldots I_n \ldots I_N$ included in the search window 500.

By using the weights, the weighted averaging unit 703 may perform a weighted averaging for all signals included in the search window 500, and thereby remove noise from the target signal 401. The weighted averaging can be performed using Equation 3 shown below.

$$I'_R = \frac{1}{w}\sum_{n=1}^{N} w_n \cdot I_n$$

$$w = \sum_{n=1}^{N} w_n$$

[Equation 3]

Here, $I'_R$ is the target signal with noise removed, and w is the sum of weights for all signals included in the search window 500.

Thus, the noise removal apparatus 100 can select all of the signals in the search window as target signals and remove noise for all signals.

Figure 8:
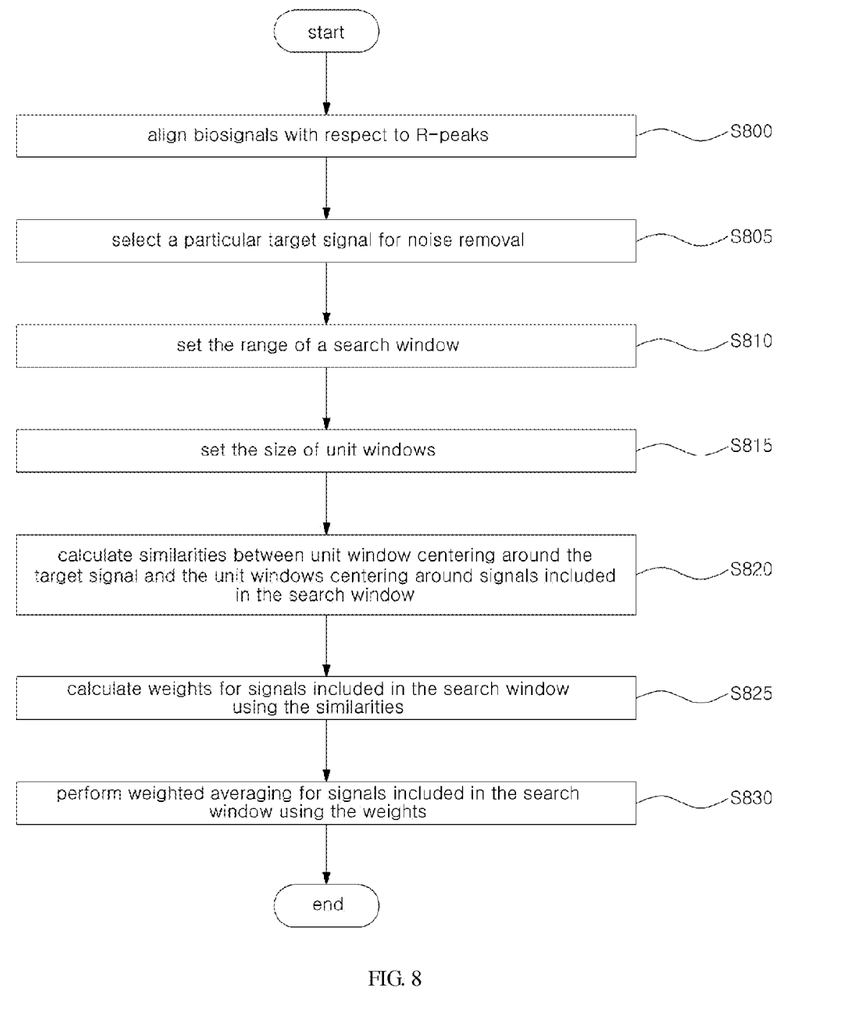
FIG. 8 is a flowchart illustrating the overall flow of a method for removing noise according to an embodiment of the invention.

FIG. 8 is a flowchart illustrating the overall flow of a method for removing noise according to an embodiment of the invention.

The operation at each step is described below in more detail with reference to FIG. 8.

First, in step S800, the alignment unit 301 may separate the biosignals, measured at the biosignal measuring unit 101 for a particular period of time, into certain areas centering around the R peaks, and may align the separated biosignals with respect to the R peaks.

In step S805, the selection unit 103 may select a particular target signal, for which to perform noise removal, from among the signals included in any one biosignal.

Then, in step S810, the search window setting unit 303 may set the range of a search window. To be more specific, the search window setting unit 303 may set the range of the search window to include the target signal and signals within a particular range centering around the target signal, from among the signals included in the aligned biosignals.

In step S815, the unit window setting unit 305 may set the size of a unit window by which to perform similarity calculations.

In step S820, the calculating unit 307 may calculate the similarities between the signals included in the unit window centering around the target signal and the signals included in the unit windows centering around the signals included in the search window.

Then, in step S825, the weight calculating unit 701 may calculate the weights for signals included in the search window by using the similarities calculated by the calculating unit 307.

Lastly, in step S830, the weighted averaging unit 703 may remove noise from the target signal by a weighted averaging of the signals included in the search window using the weights calculated by the weight calculating unit 701.

Figure 9:
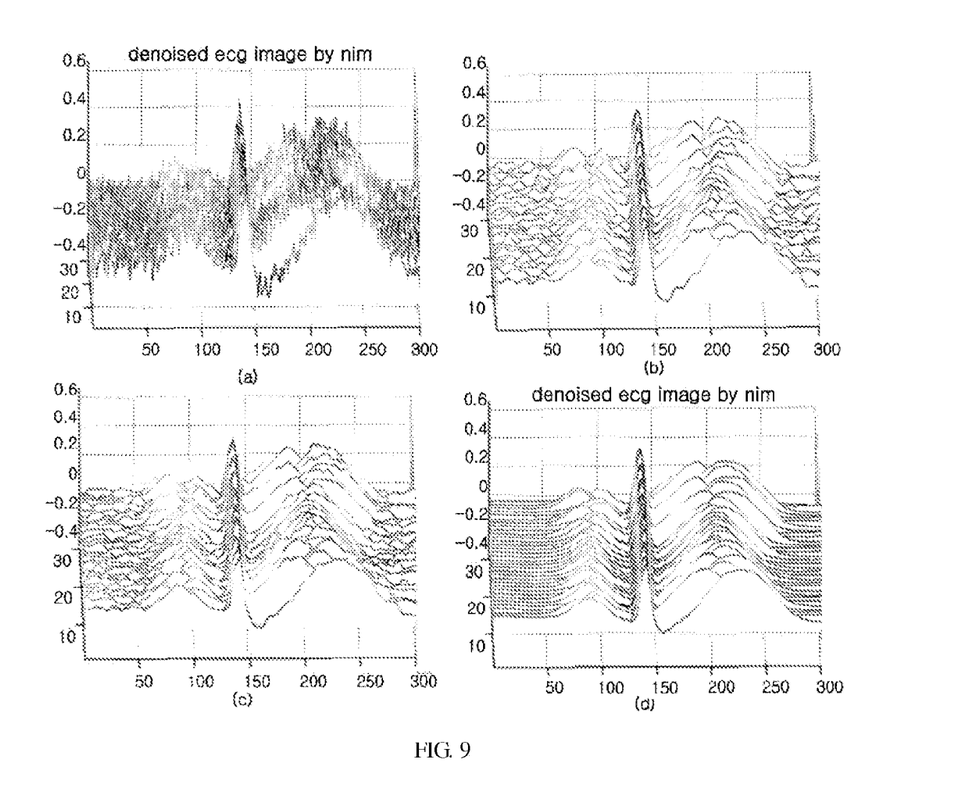
FIG. 9, FIG. 10, and FIG. 11 show graphs representing the results of removing noise from ECG signals generated by simulations, using an existing technique and a technique based on an embodiment of the invention.
Figure 10:
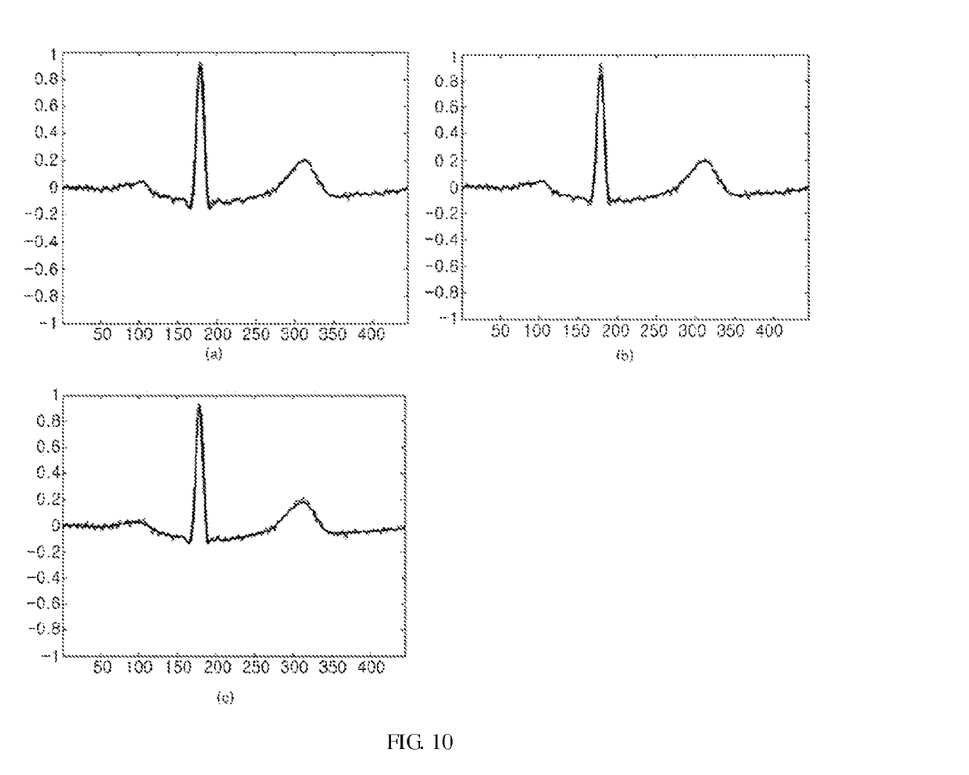
Figure 11:
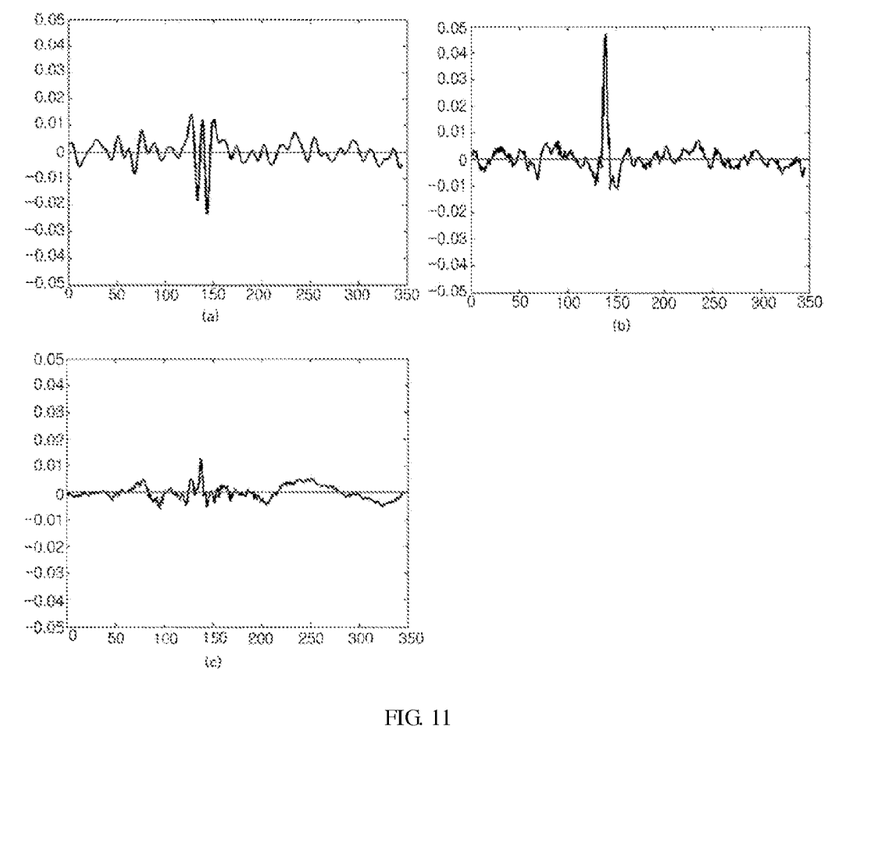

FIG. 9 through FIG. 11 show graphs representing the results of removing noise from ECG signals generated by simulations, using an existing technique and a technique based on an embodiment of the invention.

In FIG. 9, graph (a) represents multiple ECG signals generated by a simulation, graph (b) shows the signals obtained by passing the ECG signals through a band pass filter to remove noise, graph (c) shows the signals obtained by passing the ECG signals through a bilateral filter to remove noise, and graph (d) shows the signals obtained by subjecting the ECG signals to a noise removal method according to an embodiment of the invention.

In FIG. 9, comparing the signals of graph (a) with the signals of graphs (b) through (d), it can be seen that noise has been removed from the signals most effectively in graph (d), where a noise removal method according to an embodiment of the invention has been applied.

Graph (a) of FIG. 10 shows a signal extracted from graph (b) of FIG. 9, graph (b) of FIG. 10 shows a signal extracted from graph (c) of FIG. 9, and graph (c) of FIG. 10 shows a signal extracted from graph (d) of FIG. 9.

Referring to FIG. 10, it can be seen that the signal in graph (c), where the noise removal method according to an embodiment of the invention has been applied, has the smoothest curve compared with the other signals and has the noise removed with the least distortion to the P-wave, QRS-complex, and T-wave waveforms of the ECG signal.

Graph (a) of FIG. 11 shows an average error signal of the signal shown in graph (a) of FIG. 10, graph (b) of FIG. 11 shows the error rate of signal shown in graph (b) of FIG. 10, and graph (c) of FIG. 11 shows the error rate of the signal shown in graph (c) of FIG. 10.

In the graphs of FIG. 11, values closer to 0 represent smaller error. In graph (a) of FIG. 11, it can be seen that the error is uniformly distributed over all areas, and in graph (b) of FIG. 11, it can be seen that the error is especially large in the area of the QRS-complex waveform.

However, in graph (c) of FIG. 11, where the noise removal method according to an embodiment of the invention has been applied, it can be seen that there is smaller error compared with the other graphs.

Figure 12:
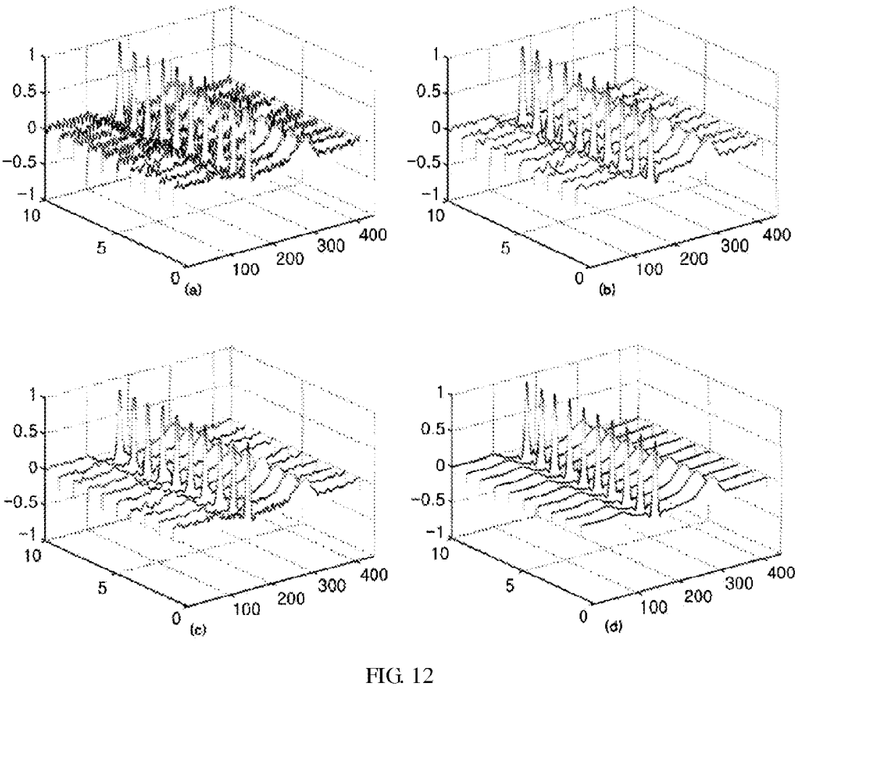
FIG. 12 shows graphs representing the results of removing noise from actual measured ECG signals, using an existing technique and a technique based on an embodiment of the invention.

FIG. 12 shows graphs representing the results of removing noise from actual measured ECG signals, using an existing technique and a technique based on an embodiment of the invention.

Graph (a) of FIG. 12 shows multiple actually measured ECG signals, graph (b) of FIG. 12 shows the signals with noise removed by passing the ECG signals through a band pass filter, graph (c) of FIG. 12 shows the signals with noise removed by passing the ECG signals through a bilateral pass filter, and graph (d) of FIG. 12 shows the signals with noise removed by subjecting the ECG signals to a noise removal method according to an embodiment of the invention.

Referring to FIG. 12, it can be seen that in graph (d), where a noise removal method according to an embodiment of the invention has been applied, the noise has been removed from the signals most effectively with the least amount of distortion to the waveforms of the ECG signals, compared with the other signals.

The embodiments of the present invention can be implemented in the form of program instructions that may be performed using various computer means and can be recorded in a computer-readable medium. Such a computer-readable medium can include program instructions, data files, data structures, etc., alone or in combination. The program instructions recorded on the medium can be designed and configured specifically for the present invention or can be a type of medium known to and used by the skilled person in the field of computer software. Examples of a computer-readable medium may include magnetic media such as hard disks, floppy disks, magnetic tapes, etc., optical media such as CD-ROM's, DVD's, etc., magneto-optical media such as floptical disks, etc., and hardware devices such as ROM, RAM, flash memory, etc. Examples of the program of instructions may include not only machine language codes produced by a compiler but also high-level language codes that can be executed by a computer through the use of an interpreter, etc. The hardware mentioned above can be made to operate as one or more software modules that perform the actions of the embodiments of the invention, and vice versa.

While the present invention has been described above using particular examples, including specific elements, by way of limited embodiments and drawings, it is to be appreciated that these are provided merely to aid the overall understanding of the present invention, the present invention is not to be limited to the embodiments above, and various modifications and alterations can be made from the disclosures above by a person having ordinary skill in the technical field to which the present invention pertains. Therefore, the spirit of the present invention must not be limited to the embodiments described herein, and the scope of the present invention must be regarded as encompassing not only the claims set forth below, but also their equivalents and variations.

What is claimed is:

1. An apparatus for removing noise from biosignals measured for a particular period of time, the apparatus comprising:
   a selection unit configured to select a target signal from a plurality of the biosignals;
   a similarity calculating unit configured to calculate a similarity between the target signal and other biosignals,
   wherein the similarity calculating unit comprises,
   an alignment unit configured to aligning the biosignals with respect to an R peak of a QRS complex wave form included in the biosignals,
   a search window setting unit configured to set a range of a search window to include the target signal and biosignals within a particular range centering around the target signal,
   a unit window setting unit configured to set a size of a unit window within the search window, and
   a calculating unit configured to calculate a similarity between signals included in a first unit window centering around the target signal and signals included in a second unit window centering around the other biosignals in the search window,
   wherein the calculating unit calculates the similarity between the target signal and the other biosignals based on a sum of absolute deviation (SAD) between the first unit window and the second unit window for each of the other biosignals; and
   a noise removal unit configured to remove noise from the target biosignal by using the similarity, wherein the noise removal unit comprises,
   a weight calculating unit configured to calculate weights for the biosignals in the search window respectively by using the similarity, and
   a weighted averaging unit configured to calculate a weighted average of the biosignals in the search window by using the weights and to remove noise from the target signal based on the weighted average of the biosignals.

2. The apparatus of claim 1, wherein the target signal is an electrocardiogram (ECG) signal, and the ECG signal includes a P-wave, the QRS-complex, and a T-wave waveform.

3. The apparatus of claim 2, wherein the weights used for calculating the weighted average is determined as follows:

$$w_n = e^{-SAD_n/\beta},$$

wherein $w_n$ is the weight for a biosignal $I_n$, e is Euler's number, $\beta$ is a constant for adjusting degree of noise removal, and $SAD_n$ is the similarity between the biosignal $I_n$ and the target signal $I_R$.

4. The apparatus of claim 3, wherein the alignment unit is configured to separate the biosignals based on a preset area centering around the R peak and is configured to align the separated biosignals with respect to the R peak.

5. The apparatus of claim 3, wherein the search window setting unit sets the range of the search window differently according to a type of waveform to which the selected target signal belongs, and
   the unit window setting unit sets the size of the unit window differently according to the type of waveform to which the selected target signal belongs.

6. A method for removing noise from biosignals measured for a particular period of time, the method comprising:
   calculating a similarity between a target signal from the biosignals and other biosignals, wherein the calculating of the similarity comprises:
   aligning the biosignals with respect to an R peak of a QRS complex waveform included in the biosignals;
   selecting the target signal for noise removal from the biosignals;
   setting a range of a search window to include the target signal and biosignals within a particular range centering around the target signal from the biosignals included in the aligned biosignals;
   setting a size of a unit window within the search window for the calculating of similarity; and
   calculating a similarity between signals included in a first unit window centering around the target signal and signals included in a second unit window centering around the other biosignals in the search window,
   wherein a sum of absolute deviation (SAD) between the first unit window and the second unit window for each of the other biosignals is used to calculate the similarity between the target signal and the other biosignals, and removing noise from the target signal by using the similarity,
   wherein removing of the noise comprises:
   calculating weights of the biosignals included in the search window respectively by using the similarity,
   calculating a weighted average of the biosignals in the search window by using the weights, and
   removing the noises from the target signal based on the weighted average of the biosignals.

7. The method of claim 6, wherein the target signal is an electrocardiogram (ECG) signal including a P-wave, the QRS-complex, and a T-wave waveform.

8. The method of claim 7, wherein the weights used for calculating the weighted average is determined as follows:

$$w_n = e^{-SAD_n/\beta},$$

wherein $w_n$ is the weight for a biosignal $I_n$, e is Euler's number, $\beta$ is a constant for adjusting degree of noise removal, and $SAD_n$ is the similarity between the biosignal $I_n$ and the target signal $I_R$.

9. The method of claim 8, wherein the target signal is selected from signals belonging to the P-wave, the QRS-complex, and the T-wave waveforms, and the setting of the range of the search window comprises setting the range of the search window differently according to a type of waveform to which the selected target signal belongs.

10. The method of claim 9, wherein the setting of the size of the unit window comprises setting the size of the unit window differently according to the type of waveform to which the selected target signal belongs.

* * * * *